(12) United States Patent
Kubota

(10) Patent No.: US 6,815,199 B1
(45) Date of Patent: Nov. 9, 2004

(54) SPECIMEN PROCESSING CONTAINER, AND CONTAINER MAIN BODY AND COVER BODY FORMING THE SPECIMEN PROCESSING CONTAINER

(75) Inventor: Tomisada Kubota, Tokyo-To (JP)

(73) Assignee: Sakura Finetechnical Co., Ltd., Tokyo-To (JP)

( * ) Notice: Subject to any disclaimer, the term of this patent is extended or adjusted under 35 U.S.C. 154(b) by 321 days.

(21) Appl. No.: 09/868,561

(22) PCT Filed: May 31, 2000

(86) PCT No.: PCT/JP00/03512

§ 371 (c)(1),
(2), (4) Date: Jun. 19, 2001

(87) PCT Pub. No.: WO01/29533

PCT Pub. Date: Apr. 26, 2001

(30) Foreign Application Priority Data

Oct. 19, 1999 (JP) ......................................... 11-296806

(51) Int. Cl.$^7$ ................................................ C12M 1/00
(52) U.S. Cl. ............................... 435/307.1; 435/305.4; 422/300; 422/102; 220/305; 220/323
(58) Field of Search .......................... 435/307.1, 305.4, 435/288.3, 283.1, 284.1, 40.5, 40.52; 422/99, 102, 104, 300, 297; 220/305, 323, 784, 835, 350, 213, 4.21, 786, 788

(56) References Cited

U.S. PATENT DOCUMENTS

| | | | | |
|---|---|---|---|---|
| 3,766,953 A | * | 10/1973 | Wilson | ........................ 220/326 |
| 4,034,884 A | | 7/1977 | White | ........................... 220/8 |
| 4,810,066 A | * | 3/1989 | Awakowicz et al. | ......... 359/237 |
| 5,084,251 A | * | 1/1992 | Thomas | ....................... 422/300 |
| 5,752,615 A | * | 5/1998 | Hofmann et al. | ........... 220/324 |
| 5,843,700 A | | 12/1998 | Kerrod et al. | .............. 435/40.5 |
| 5,950,814 A | * | 9/1999 | Lindberg et al. | ................ 206/6 |

FOREIGN PATENT DOCUMENTS

| | | |
|---|---|---|
| JP | 51118531 | 10/1976 |
| JP | 3179232 | 8/1991 |
| JP | 473841 | 6/1992 |
| JP | 10246691 | 9/1998 |
| JP | 10281953 | 10/1998 |

\* cited by examiner

*Primary Examiner*—William H. Beisner
(74) *Attorney, Agent, or Firm*—Ladas & Parry

(57) ABSTRACT

A lid body 200 is divided, on its front side, into three parts, that is, a pair of first movable parts 220 in the form of curved plates on both sides of the body and a second movable part 230 in the form of a flat plate in the middle of the body. A container body 100 is provided with a front engagement member 131 which is displaceable in front and in the rear of the body 100. The first movable parts 220 have front engagement members 221 formed at their front ends to be engageable with the front engagement member 131. While, the second movable part 230 has a disengagement member 231 formed at the front ends. The first movable parts 220 on elastic deformation are engaged with the front engagement member 131. When the second movable part 230 is subjected to depression of its upper face at the front end so that the disengagement member 231 causes the front engagement member 131 to be displaced forward, the engagement of the front engagement member 131 with the front engagement members 221 is released. As a result, the first movable parts 220 are separated from the container body due to their elastic restoration.

24 Claims, 12 Drawing Sheets

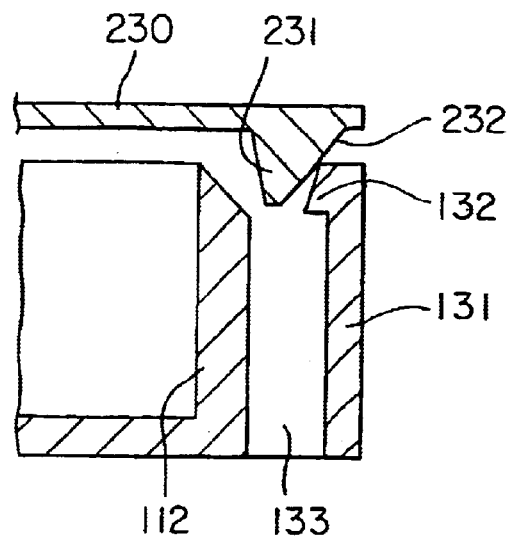
F I G. 6
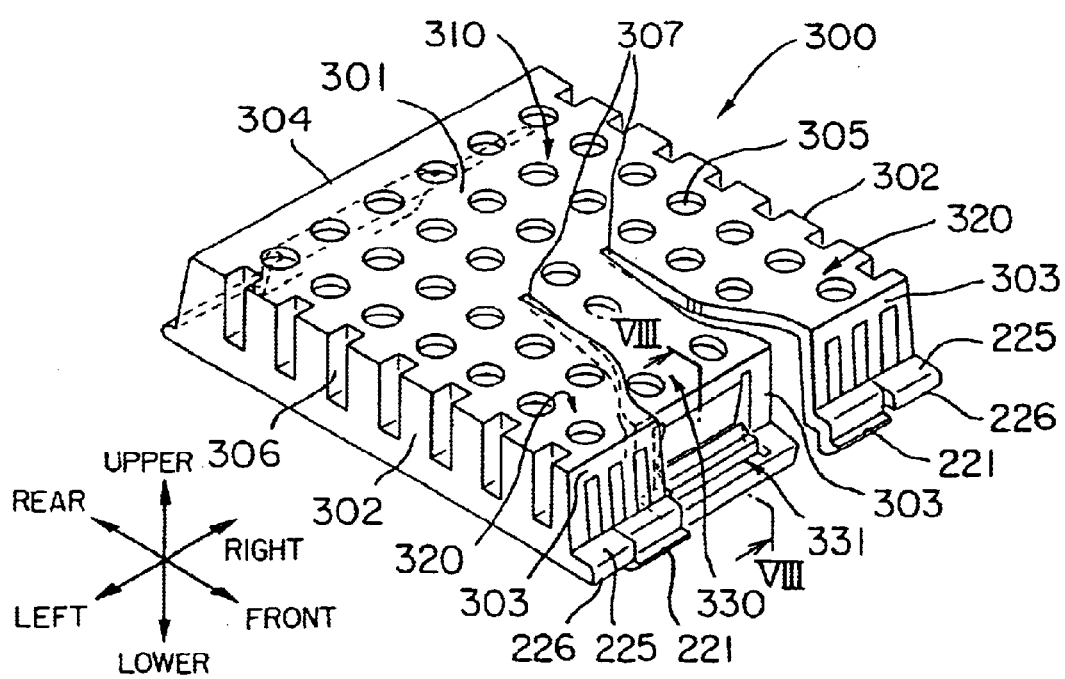
F I G. 7

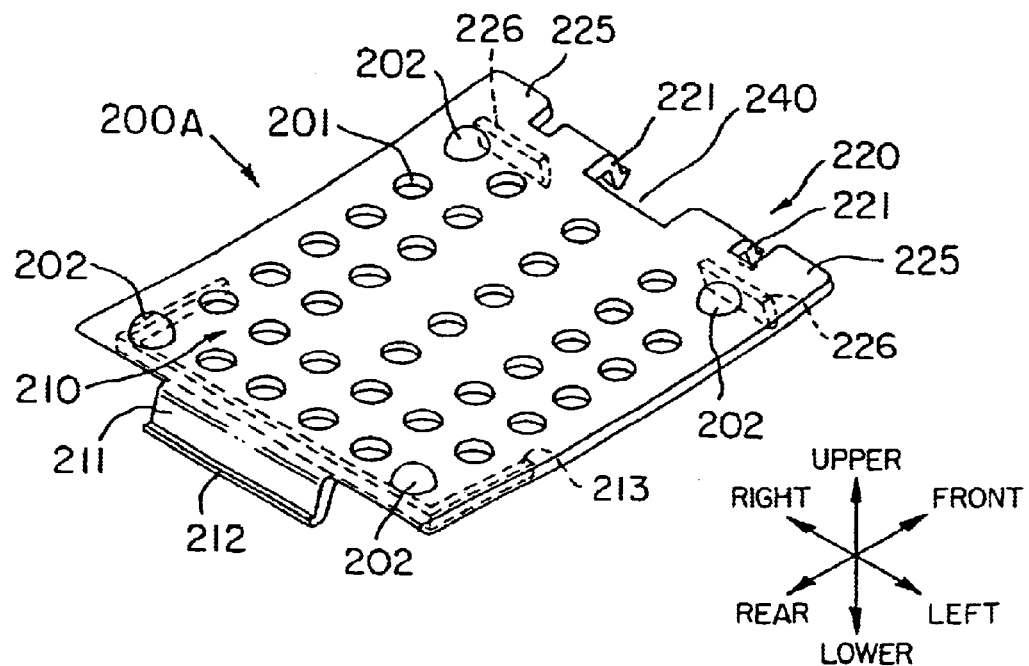
F I G. 12 (a)
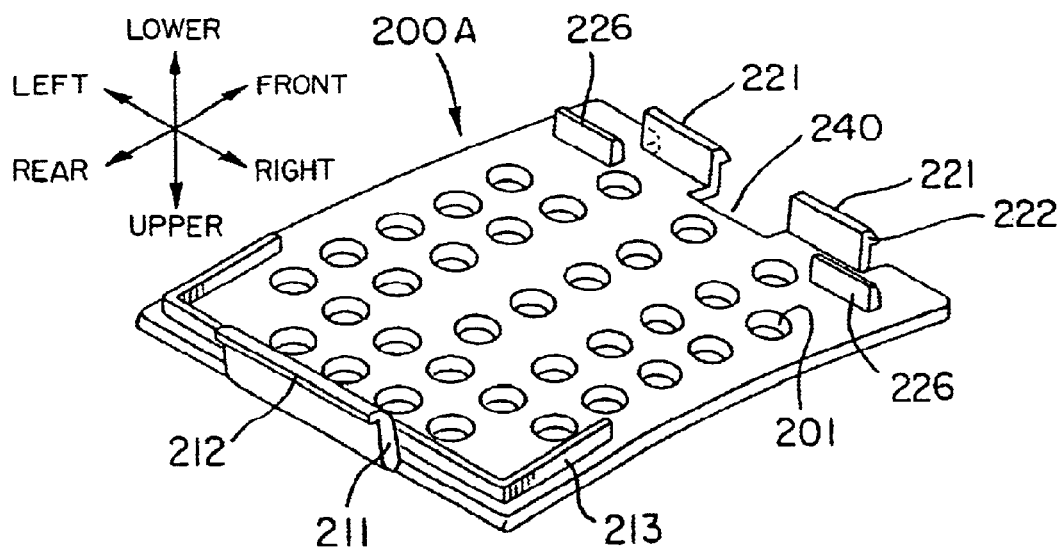
F I G. 12 (b)

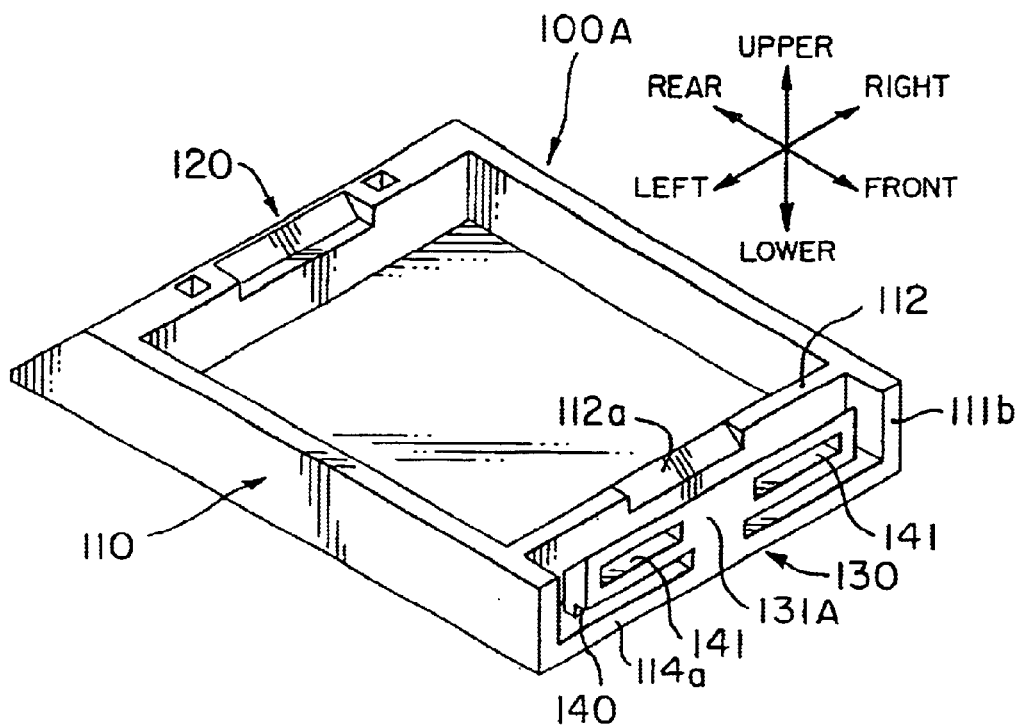
F I G. 13(a)
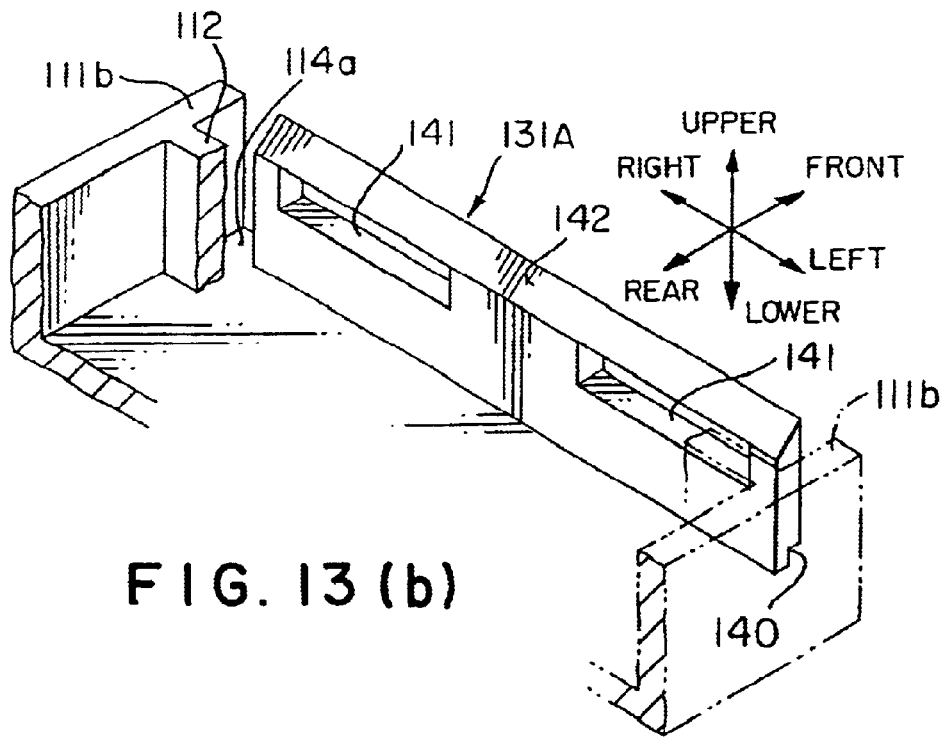
F I G. 13(b)

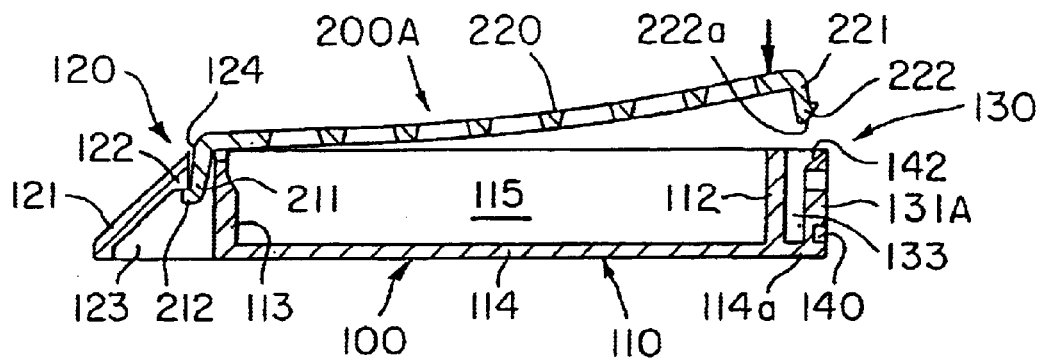
F I G. 14 (a)
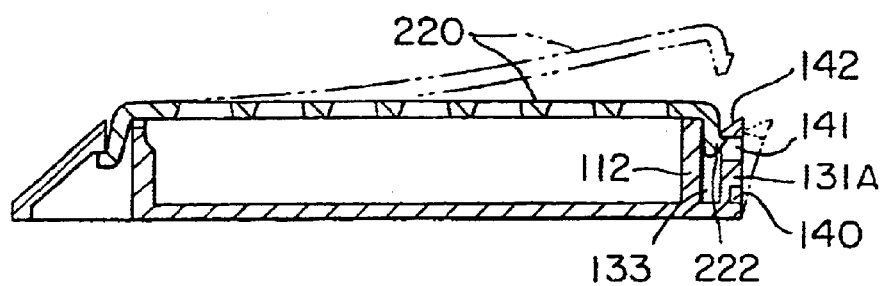
F I G. 14 (b)
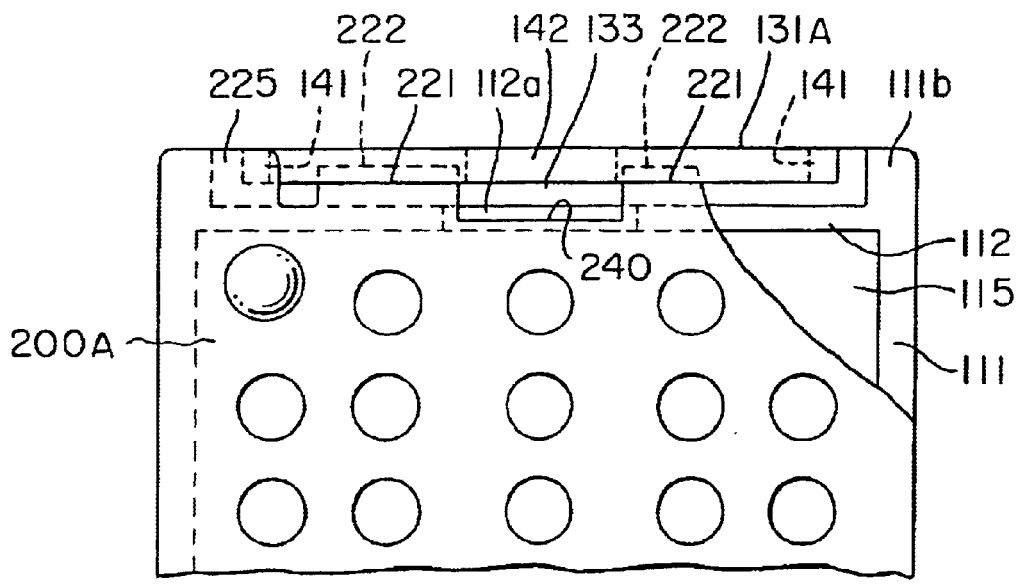
F I G. 15

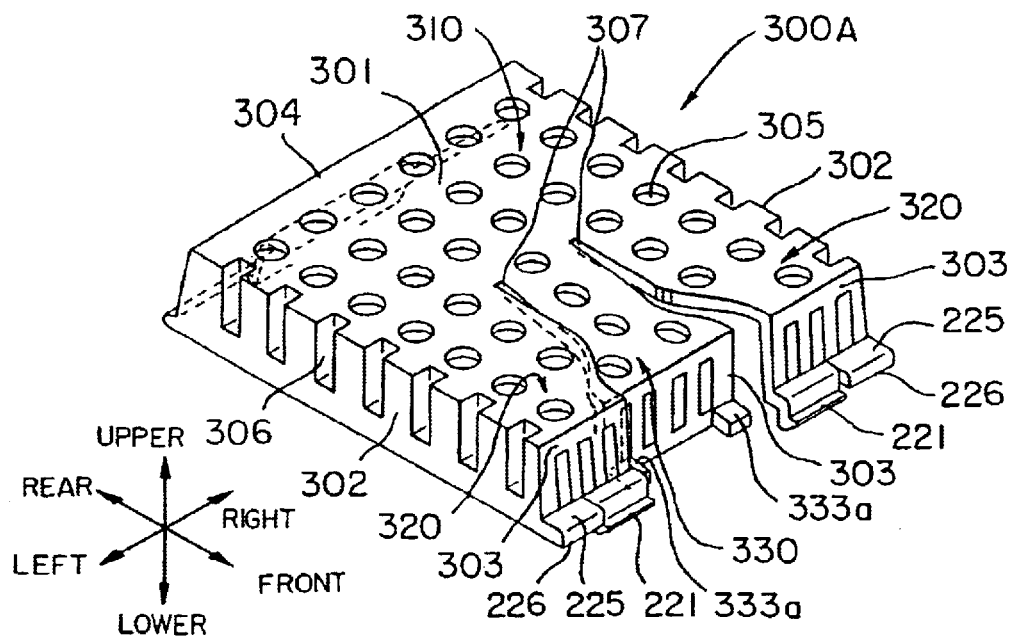
F I G. 16
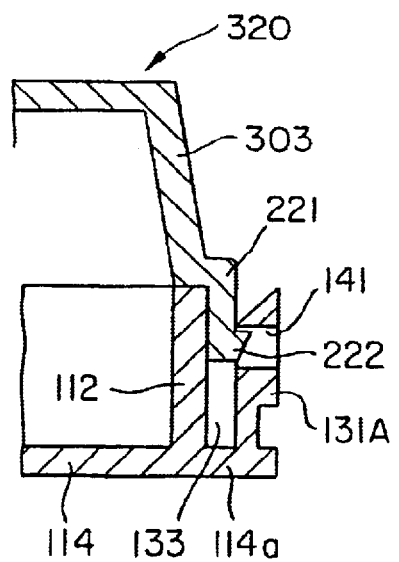
F I G. 17(a)
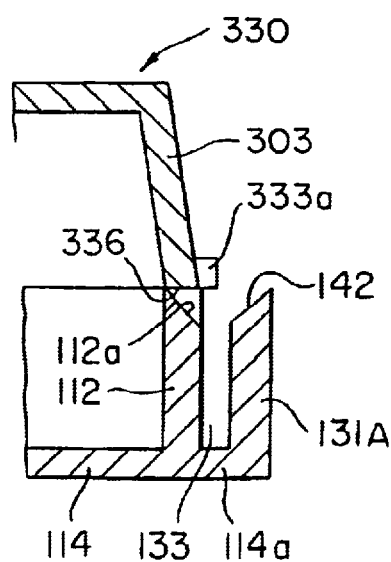
F I G. 17(b)

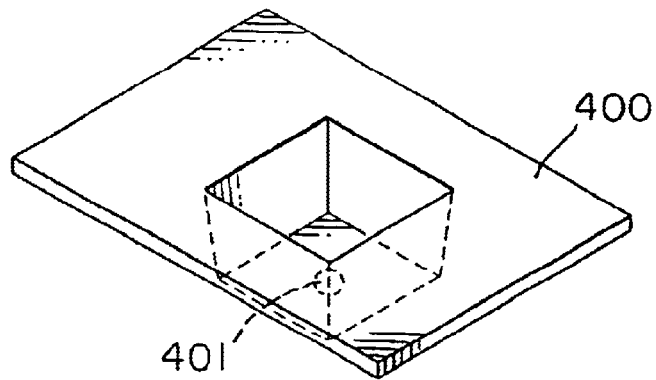
F I G. 20 (a)
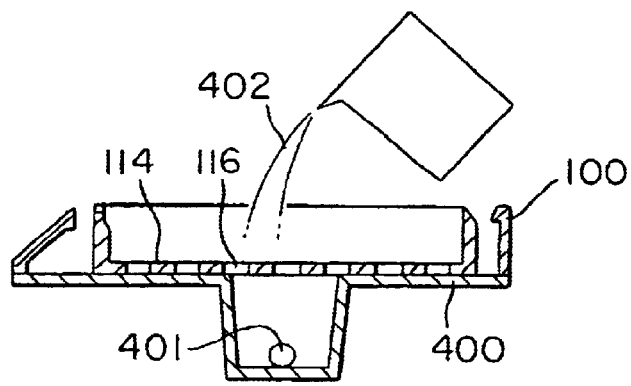
F I G. 20 (b)
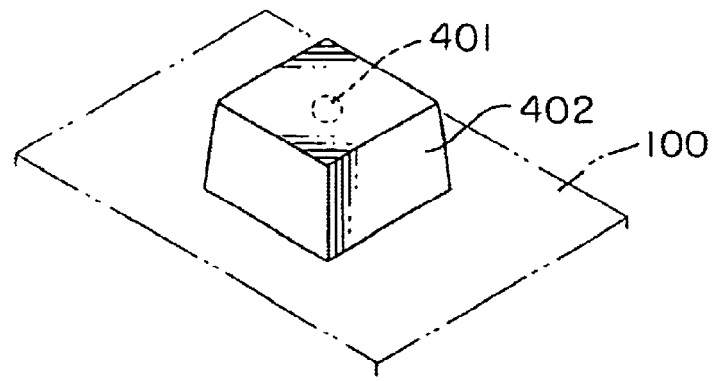
F I G. 20 (c)

SPECIMEN PROCESSING CONTAINER, AND CONTAINER MAIN BODY AND COVER BODY FORMING THE SPECIMEN PROCESSING CONTAINER

This application is a 371 of PCT/JP00/03512 filed May 31, 2000.

The present invention relates to a sample processing container for accommodating samples therein to supply them to a variety of processes, such as chemical processing.

BACKGROUND OF THE INVENTION

For the microscopic observation, the samples are usually subjected to chemical processing in advance of the observation. In this chemical processing, the samples are handled while being accommodated in a processing container for the samples in viewpoints of prevention of damage and missing, clearness in classification, etc. The processing container has a container body called. "cassette" in general and a lid body for the container body.

In one process carried out on the last stage of the sample processing, the container accommodating the sample is dipped into molten paraffin of approx. 60° C. in order to allow paraffin to permeate the sample.

After completing this process, the lid body is opened and the sample is taken out of the container. Hitherto, this operation has been carried out by means of an operator's hand. However, the operator was apt to have a hard time to handle the container for its hotness. Although it is expected to prepare an exclusive tool for opening the lid, it would be also trouble to fit the device to the container and furthermore, the total cost would be increased.

SUMMARY OF THE INVENTION

With respect to the above, the object of the present invention is to provide a sample processing container which allows the lid body to be easily opened by the operator's performance of simple manipulation without using any exclusive tool.

In order to accomplish the above object, the present invention provides a sample processing container which includes: a container body having an accommodating part for accommodating a sample therein, a front engagement part arranged at a front of the accommodating part and a rear engagement part arranged at a rear of the accommodating part; and a lid body whereas at least a part thereof is curved, the lid body having a front side and a rear side, the rear side of the lid body being provided with a front engagement member which is engageable with the rear engagement part of the container body and the front side of the lid body being provided with a rear engagement member which is engageable with the front engagement part of the container body; wherein engagement of the front and rear engagement members of the lid body with the front and rear engagement parts of the container body respectively allows the lid body to be fitted to the container body and causes the lid body to be elastically deformed into either a plane state or a reduced-curved state in which a degree of curvature of the lid body is reduced; and wherein releasing the engagement of the front engagement member of the lid body with the front engagement part of the container body allows the lid body to be restored elastically, so that the front side of the lid body is separated from the container body.

The present invention also provides a sample processing container which includes: a container body having an accommodating part for accommodating a sample therein, a front engagement part arranged at a front of the accommodating part and a rear engagement part arranged at a rear of the accommodating part; and a lid body having a base part provided with a rear engagement member engageable with the rear engagement part of the container body, and first and second movable parts connected in parallel to a front side of the base part with respect to a left-and-right direction of the sample processing container; wherein the first movable part is provided with a front engagement member engageable with the front engagement part of the container body, and the second movable part is provided with a disengagement member acting on the front engagement part of the container body thereby to release an engagement between the front engagement part and the front engagement member; and wherein the container body and the lid body are configured so that: the front engagement member engages with the front engagement part under condition that the first movable part is deformed elastically; and when an engagement of the front engagement member with the front engagement part is released by the disengagement member, the first movable part is restored elastically so that the front engagement member is apart from the front engagement part of the container body.

The present invention also provides a sample processing container which includes: a container body having an accommodating part for accommodating a sample therein, a front engagement part arranged at a front of the accommodating part and a rear engagement part arranged at a rear of the accommodating part; and a lid body having a base part provided with a rear engagement member engageable with the rear engagement part of the container body, and immovable and movable parts connected in parallel to a front side of the base part with respect to a left-and-right direction, the immovable part being substantially immovable to the base part, the movable part being movable to the base part, the immovable part being provided with a front engagement member which is engageable with the front engagement part of the container body; wherein the container body and the lid body are configured so that: upon movement of the immovable part toward the front engagement part of the container body, the immovable part engages with the front engagement part of the container body under condition that the movable part is deformed elastically; and when an engagement of the front engagement member of the immovable part with the front engagement part of the container body is released by the disengagement member, the movable part is restored elastically so that the front engagement member of the immovable part is apart from the front engagement part of the container body.

The present invention is described in detail referring the attached drawings in which the preferred embodiments are illustrated.

BRIEF DESCRIPTION OF THE DRAWINGS

FIG. 6 is a view showing an area VI of FIG. 5 in detail;

FIG. 7 is a perspective view showing the sample processing container in accordance with the second embodiment of the present invention, showing the lid body only;

FIG. 12 is a perspective view showing the sample processing container in accordance with the third embodiment of the present invention, showing the lid body only;

FIG. 13 is a perspective view showing the sample processing container in accordance with the third embodiment of the present invention, showing the container body only;

FIG. 14 is a sectional view of the sample processing container including a front engagement member, for explanation of the operation of the container;

FIG. 15 is a top plan view of the sample processing container where the lid is fitted to the container body;

FIG. 16 is a perspective view showing the sample processing container in accordance with the fourth embodiment of the present invention, showing the lid only;

FIG. 17 are views for explanation of the operation of the sample processing container; FIG. 17(a) is a sectional view including the immovable part and FIG. 17(b) is a sectional view including the movable part;

FIG. 20 are views for explanation of the using method of the sample processing container.

DESCRIPTION OF THE PREFERRED EMBODIMENTS

Embodiments of the present invention will be described below, with reference to the drawings.

[1st. Embodiment]

The first embodiment of the invention will be described with reference to FIGS. 1 to 6. In order to simplify the explanation, the left-and-front side of FIG. 1 is called "rear" in the specification, the right-and-back side of the figure "front", the right-and-front side of the figure "left", the left-and-backside of the figure "right", the upside of the figure "upper", and the downside of the figure is called "lower", respectively.

Figure 1:
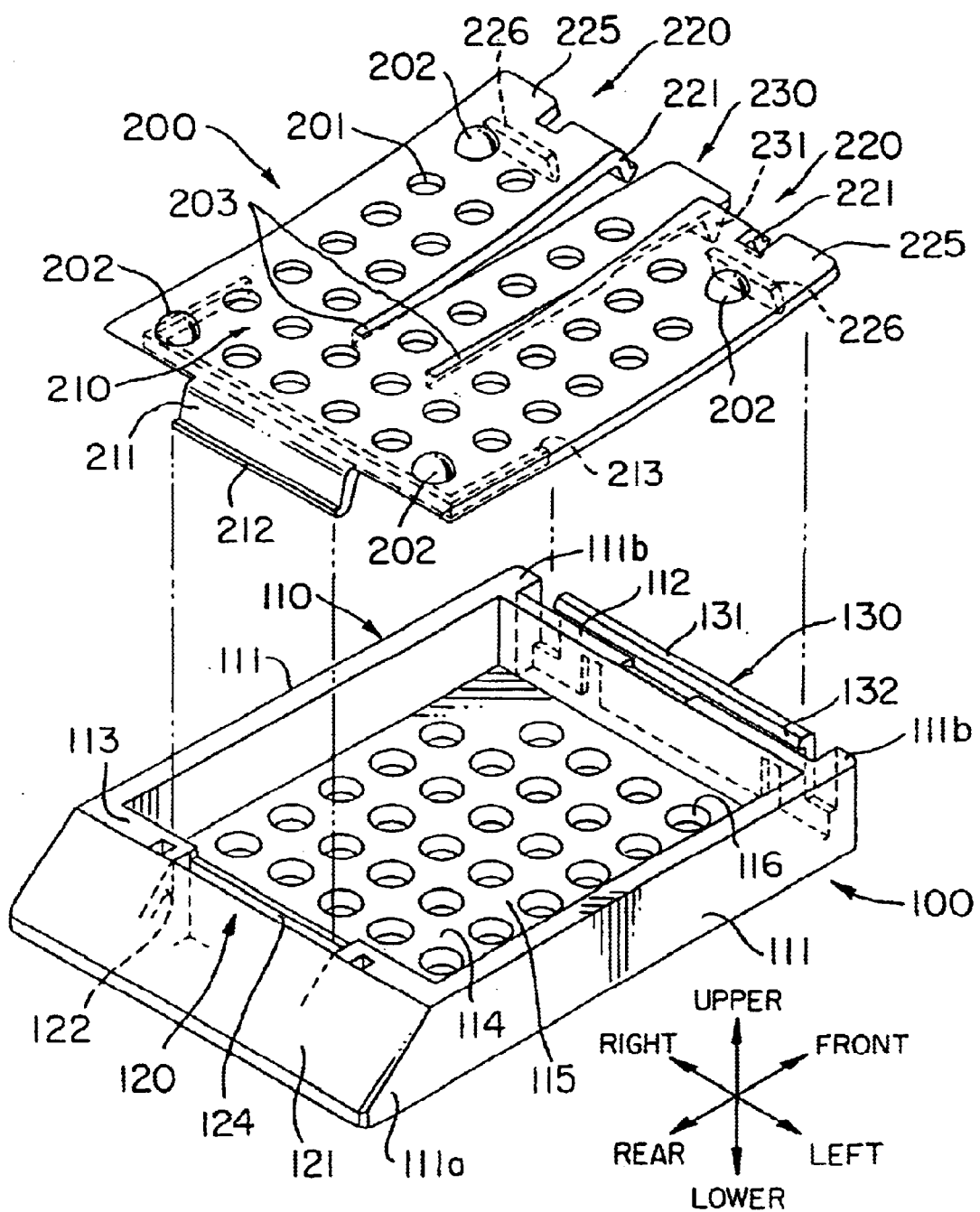
FIG. 1 is a perspective view showing a sample processing container in accordance with the first embodiment of the present invention.

As shown in FIG. 1, the sample processing container includes a container body 100 and a lid body 200 detachably fitted to the container body 100. The container body 100 and the lid body 200 are together shaped to be bilaterally symmetrical. The container body 100 and the lid body 200 are made of resinous material and integrally formed by means of a technique such as injection molding. Preferably, polyacetal is used as the resinous material.

As shown in FIG. 1, the container body 100 has an accommodating part 110 for accommodating a sample, a rear engagement part 120 arranged at the rear of the accommodating part 110 and a front engagement part 130 arrange at a front of the accommodating part 110.

First, the constitution of the accommodating part 110 will be described hereinafter. As shown in FIG. 1, the accommodating part 110 is formed by left and right sidewalls 111 in pairs, a front wall 112, a rearwall 113 and a bottom wall 114. These walls 111–114 define a generally rectangular-shaped sample accommodating space 115 whose upside is opened. On the bottom wall 114, a plurality of circular through-holes 116 are formed in a grid pattern.

Next, the structure of the rear engagement part 120 will be described. As shown in FIGS. 1, 4 and 5, the rear engagement part 120 is defined by the rear wall 113 of the accommodating part 110 and a slant wall 121 joined to the rear wall 113. Left and right ends of the slant wall 121 are joined to rear extension parts 111a, 111a of the sidewalls 111, 111, respectively. The slant wall 121 is slanted to a horizontal plane with an angle of 45 degrees. The slant wall 121 is provided, on its interior top end, with a step part 122 for engagement with an engagement claw 212 of a rear engagement member 211 of the lid body 200 mentioned in detail later. The step part 122 is formed to extend in the left-and-right direction while maintaining an identical cross-section. Defined between the slant wall 120 and the rear wall 113 is a space 123 whose bottom side is opened. The rear wall 113 and the slant wall 121 are joined to each other at respective top ends thereof; nevertheless the resulting joined part is removed in the middles of the walls in the left-and-right direction, producing an opening 124. The opening 124 is formed to receive the later-described rear engagement member 211.

The constitution of the front engagement part 130 is as follows. A front engagement member 131 in the form of an upright plate and the front wall 112 of the accommodating part 110 constitute the front engagement part 130. The front engagement member 131 extends in the left-and-right direction. As shown in FIGS. 4 and 5, the front engagement member 131 is provided, at a top end thereof, with an engagement claw 132 projecting rearward for engagement with a front engagement member 221 of a first movable part 220 of the lid body 200 mentioned in detail later. The engagement claw 132 is formed to extend in the left-and-right direction while maintaining an identical cross-section.

Figure 2:
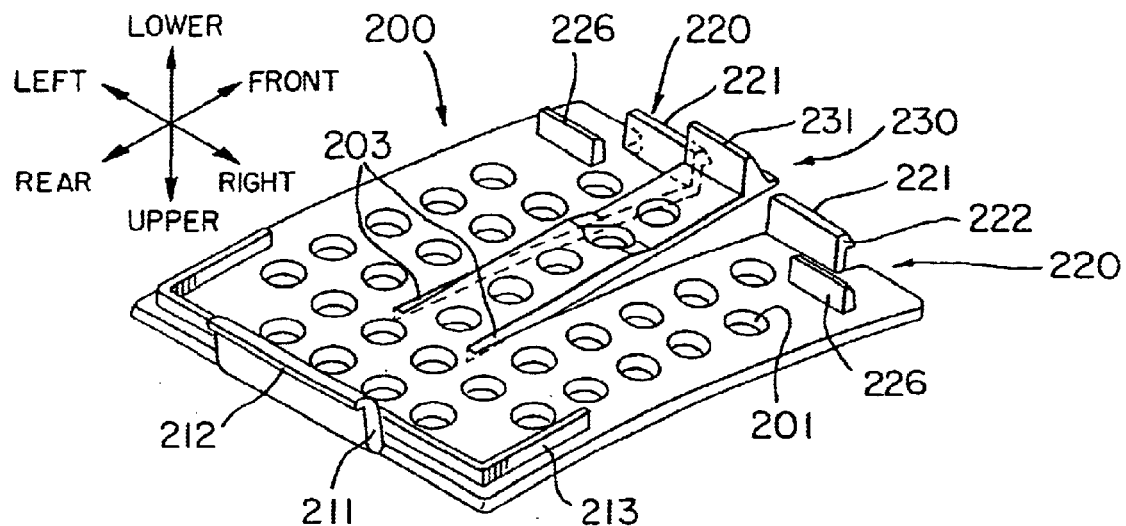
FIG. 2 is a perspective view of the underside of a lid body of FIG. 1.

As shown in FIGS. 1 and 2, the front engagement member 131 has left and right ends connected to front extension parts 111b, 111b of the sidewalls 111, 111, respectively. A gap 133 is defined between the front engagement member 131 and the front wall 112 of the accommodating part 110 (see FIGS. 4 and 5).

Figure 3:
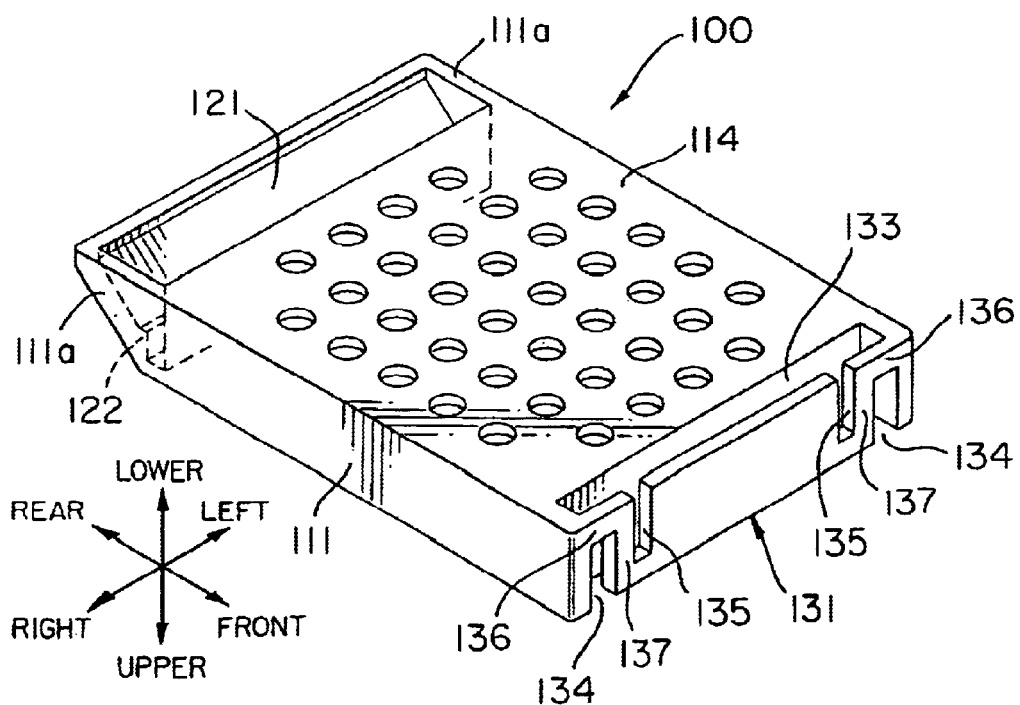
FIG. 3 is a perspective view of the underside of a container body of FIG. 1.

As shown in FIG. 3, in the vicinities of left and right ends of the front engagement member 131, there are formed slits 134, 134 which extend up and down, at bilaterally symmetrical positions of the member 131. Additionally, there are formed, inside the slits 134, 134, slits 135, 135 which extend up and down, at bilaterally symmetrical positions of the member 131. Owing to the provision of the slits 134, 135, the engagement claw 132 as an engagement element of the front engagement member 131 is connected with the front extension parts 111b, 111b of both sidewalls 111 through thin horizontal joint parts 136, 136 and vertical joint parts 137, 137, respectively. Therefore, if a force in the front-and-rear direction is applied on the engagement claw 132, the vertical joint parts 137, 137 prefer to bend rather than the other portions. Consequently, the engagement claw 132 and the front engagement member 131 close to the claw 132 are capable of smooth swing about an imaginary axis which extends in the left-and-right direction through the vertical joint parts 137, without producing any distortion in themselves. With the swing movements, the engagement claw 132 of the front engagement member 131 and the vicinities can move in the front-and-rear direction [see FIG. 4(b)].

The lid body 200 will be described below. As shown in FIGS. 1 and 2, the lid body 200 has a generally flat plate-shaped configuration. A plurality of truncated conical through-holes 201 are formed in a grid pattern on the whole surface of the lid body 200. The lid body 200 has hemispheric projections 202 formed at the four corners of the upper face of the lid body 200.

The lid body 200 comprises a base part 210 positioned on the rear side of the body, a pair of first movable parts 220, 220 and a second movable part 230. The first movable parts 220 and the second movable part 230 are together shaped in the form of tongue pieces. The second movable part 230 is interposed between the first movable parts 220, 220 in left and right. The first movable parts 220, 220 and the second movable part 230 are connected in parallel to the only one base part 210 along the left-and-right direction. That is, the parts 220, 230 are capable of moving in relation to the base part 210. In this embodiment, the lid body 200 is provided with two slits 203 formed in the front portion while leaving the base part 210, to divide the front portion into three pieces providing the first and second movable parts 220, 230.

In the constituents of the lid body 200, the base part 300 has the following structure. As shown in FIGS. 1 and 2, the base part 210 is shaped to be a substantially flat plate. At the rear end of the base part 210, the rear engagement member 211 is formed to extend downward. The rear engagement member 211 is provided, at a tip thereof, with the engagement claw 212. As shown in FIGS. 4 and 5, the rear engagement member 211 can be inserted into the space 123 between the slant wall 121 and the rear wall 113 through the opening 124 of the container body 100. Further, by engaging the engagement claw 212 with the step part 122 of the slant wall 121, it allows the rear end of the lid body 200 to engage with the container body 100. As shown in FIGS. 4 and 5, the width of the engagement claw 212 in the front-and-rear direction is smaller than the width of the opening 124 in the same direction. Therefore, it is possible to attach the rear engagement member 211 of the lid body 200 to the rear engagement part 120 of the container body 100 and also possible to detach the former from the latter with ease.

Next, the structures of the first movable parts 220 and the second movable part 230 will be described below. As shown in FIGS. 1 and 2, the second movable part 230 is shaped to be substantially flat and also formed to extend forward in a plane generally-identical to a plane containing the base part 210 of a flat plate. On the other hand, each of the first movable parts 220 is curved (or arched) as if it were gradually apart from the above plane containing the base part 210 as approaching the front end, on condition that no external force is applied on the part 220.

The so-curved first movable part 220 is capable of elastic deformation in a manner that its front end can move in directions (substantially, the upward-and-downward direction) to approach and leave the front engagement part 130 of the container body 100. Similarly, the second movable part 230 is also capable of elastic deformation in a manner that its front end can move in directions (substantially, the upward-and-downward direction) to approach and leave the front engagement part 130 of the container body 100.

The first movable parts 220 have their front ends each divided into two portions in the left-and-right direction. In these leading ends of the movable part 220, the inside end, that is, one closer to the second movable part 230 is provided with a front engagement member 221. The front engagement member 221 extends downward and has, at a lower thereof, an engagement element, i.e. an engagement claw 222 projecting forward. The front engagement members 221 can be inserted into the gap 133 between the front wall 112 and the front engagement member 131. Then, by mutually engaging the engagement claw 132 of the front engagement member 131 with the engagement claws 222 of the front engagement members 221, it allows the front end of the lid body 200 to be fixed with the container body 100 [see FIG. 4(b)].

In the leading ends of the movable part 220, the outside end, that is, one apart from the second movable part 230 is provided with a tab 225 for assisting the user's operation to open the lid body 200.

While, as shown in FIGS. 2, 5 and 6, the intermediate second movable member 230 is provided, at a tip thereof, with a wedge-shaped projection 231 (i.e. a disengagement member) having a generally triangular cross-section and projecting downward. The projection 231 is provided, on its front side, with a slant face 232.

As shown in FIGS. 2 and 5, the second movable part 230 has a thin part arranged on the rear side of the projection 231, forming a run-off 233 on the underside of the part 230. Additionally, the center top of the front wall 112 of the container body 100 is notched obliquely. Consequently, it is possible to exclude the second movable part 230 from interference with the front wall 112, which might be caused at a time of operating the part 230.

As shown in FIG. 2, on the under face of the base part 210, a square bracket-shaped projection 213 is formed to project downward. Further, each of the first movable parts 220 has a projection 226 formed on its under face to project downward and also extend in the left-and-right direction. The projection 213 abuts against the respective inner faces of the sidewalls 111, 111 and the rear wall 113 of the container body 100, while the projections 226 abuts against the inner face of the front wall 112 of the container body 100, accomplishing the positioning of the lid body 200 to the container body 100. The projection 213 further functions as rib to improve the rigidity of the base part 210. The projections 213, 226 may be altered with regard to their configuration and position providing that they can effect functions similar to those of this embodiment.

Next, a method of getting the lid body 200 on and off the container body 100 will be described below.

In order to attach the lid body 200 to the container body 100, the rear engagement members 211 of the base part 210 of the lid body 200 is inserted into the opening 124 of the container body 100, thereby to engage the step part 122 formed on the slant wall 121 with the engagement claw 212 of the rear engagement member 211.

In this state, when the lid body 200 is mounted on the top face of the container body 100, then the base part 210 and the second movable part 230 of the lid body 200 become parallel with the opening face of the container body 100 thereby to cover the upside of the accommodating part 110 of the container body 100. Then, there is established a condition where the projection 231 at the tip of the second movable part 230 touches or adjoins the upper end of the front engagement member 131 of the container body 100 while leaving a slight clearance [see FIG. 5(a) and FIG. 6]. Therefore, in such a condition, the second movable part 230 has already operated as lid for covering the accommodating part 110. On the contrary, the curved first movable members 220 are apart from the opening face of the container body 100, realizing a so-called "semi-opening" condition [see FIG. 4(a)].

Figure 4A:
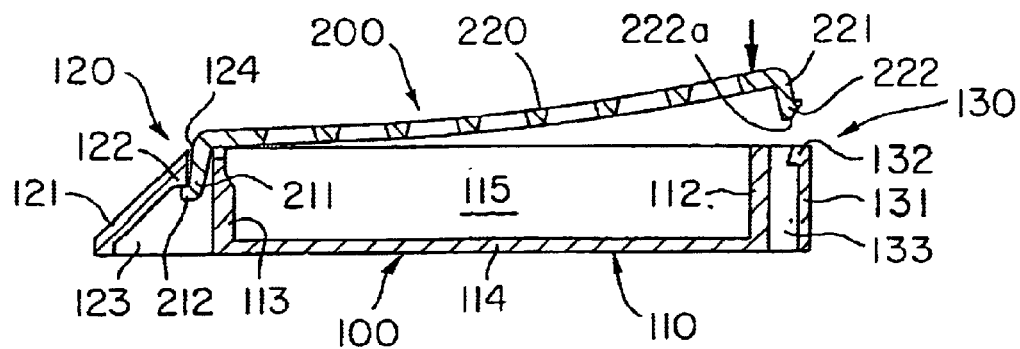
FIG. 4 are sectional views of the sample processing container including a first movable part, for explanation of the operation of the container.
Figure 4B:
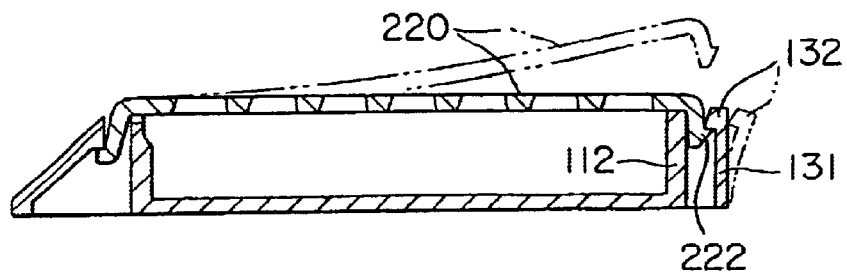
Figure 5A:
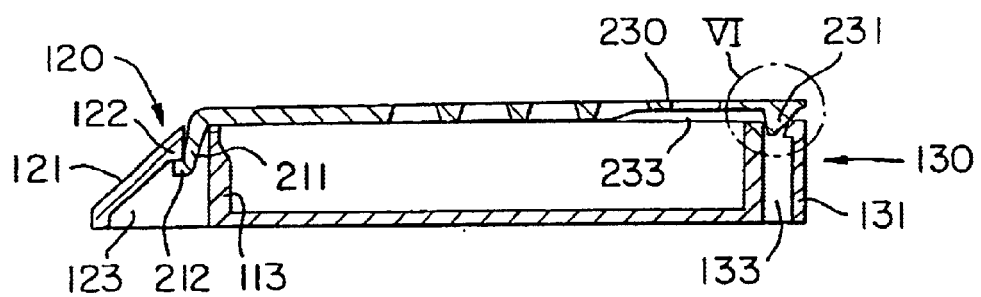
FIG. 5 are sectional views of the sample processing container including a second movable part, for explanation of the operation of the container.
Figure 5B:
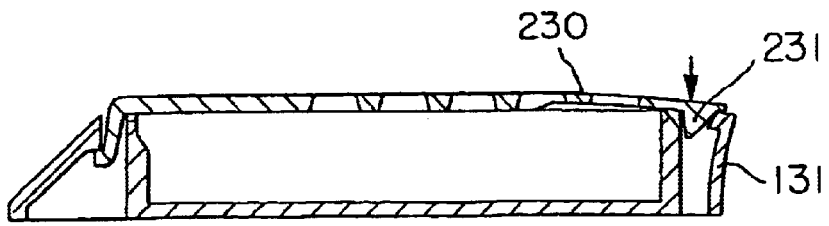

Next, the top faces of the front ends of the first movable parts 220 is depresses by tweezers, fingers or the like [see FIG. 4(b)]. Consequently, the respective engagement claws 222 of the front engagement members 221 enter into the gap 133 while their slant faces 222a urge the engagement claw 132 of the front engagement member 131 forward. After insertion of the claws 222, the front engagement member 131 recover elastically, whereby the respective engagement claws 222 of the front engagement members 221 are engaged with the engagement claw 132 of the front engagement member 131 [see FIG. 4(b)]. The under faces of the first movable parts 220 at the front ends and the rear faces of the front engagement members 221 are respectively supported by the front wall 112 of the accommodating part 110 of the container body 100.

In this way, the front engagement members 221 of the first movable parts 220 of the lid body 200 are engaged with the front engagement part 130 of the container body 100, realizing the first movable parts 220 being in the closed state. Then, the first movable parts 220 are settled in their elastically-deformed condition and also flattened substantially. The plural (two) front engagement members 221 are together engaged with the single engagement member 131 in the same manner. In this way, there can be completed an operation to fit the lid body 200 to the container body 100. When the lid body 200 is fitted to the container body 100 in the above way, the entire lid body 200 becomes a flat plate, thereby to cover the upside of the accommodating part 110.

The operation to detach the lid body 200 from the container body 100 will be described. First, the top of the second movable part 230 at the front end is depressed by tweezers or the like [see arrow of FIG. 5(b)]. During the descent of the projection 231 of the second movable part 230, the slant face 232 at the front of the projection 231 comes into contact with the top of the front engagement member 131 (i.e. the engagement claw 132 in the embodiment) of the container body 100 thereby to bend the member 131 elastically while moving the top of the member 131, that is, the engagement claw 132 forward [see FIG. 5(b)].

With the deformation of the front engagement member 131, there is simultaneously released the engagement between the engagement claw 132 of the front engagement member 131 and the claws 222 of the front engagement members 221 of the first movable parts 220, as shown with two-dot chain line of FIG. 4(b). As a result, the first movable parts 220, which have been elastically deformed and engaged with the front engagement part 130, return the "semi-opening" position indicated by two-dot chain line of FIG. 4(b) and are separated from the container body 100 upward. Under this situation, it is possible to greatly open the lid body 200 by pinching the tabs 225 of the first movable parts 220 by means of tweezers or the like. By continuously withdrawing the rear engagement members 211 of the lid body 200 out of the opening 124 of the container body 100 while taking the tabs 225 between the tweezers, it allows the lid body 200 to be separated from the container body 100 perfectly.

As mentioned above, according to this embodiment, the lid body 200 can be easily put on and taken off the container body 100 with an user's single action. It is expected that if any force in the oblique or left-and-right direction is required to open the lid body 100, the conventional sample processing container would be disadvantageously moved to make the operation hard because of its light-weight structure. According to this embodiment, since the lid body 100 can be opened by only applying a downward force on the container of the embodiment, there is no possibility that the container is unexpectedly moved before opening the lid body, effecting an advantage of making the user's operation with ease.

It should be noted that, although the drawings of this embodiment illustrate the structure where the front engagement part 131 of the container body 100 is displaced by the butting of the projection 231 of the second movable part 230 against only the front engagement member 131, the present invention is not limited to this arrangement. Thus, in the modification, the projection 231 may be formed so as to move the front engagement member 131 while butting not only the member 131 but also the front wall 112. Then, the projection 231 operates as a wedge for expanding the gap 133.

The cross section of the projection 231 is not limited to triangular shape of the embodiment. Further, the projection 231 is not necessarily provided with the slant face 232. Alternatively, the front engagement member 131 may include a slant face. That is, at least either one of the projection 231 and the front engagement member 131 has only to be equipped with means that the front engagement member 131 butting the projection 231 could be displaced in front by depressing the second movable part 230 downward.

Although the first movable parts 220 are together engaged with the front engagement part 130 by the mutual engagement of claw-shaped members (the engagement claws 132, 222) in this embodiment, the present invention is not limited to only the shown engagement form. That is, there may be adopted an arrangement where the front engagement member 131 has, in place of the engagement claw 132, a recess formed to extend in the left-and-right direction and the first movable parts 220 have respective projections formed for engagement with the recess. In short, any structure will do so long as the front engagement member 131 can prevent the first movable parts 220 upon elastically deformation from being displaced upward and further, the engagement of the movable parts 220 with the first engagement part 130 can be released by moving the front engagement member 131 in the front-and-rear direction.

[2nd. Embodiment]

With reference to FIGS. 7 to 11, the second embodiment of the invention will be described. The second embodiment differs from the first embodiment in the provision of a lid body 300 in place of the above lid body 200 of the first embodiment. The second embodiment is similar to the first embodiment in terms of the structure of the container body 100 and therefore, the redundant descriptions about the container body 100 are omitted.

As shown in FIG. 7, the lid body 300 has a top wall 301, a pair of sidewalls 302, 302, a front wall 303 and a rear wall 304, in the form of a box having its underside opened.

On the entire surface of the top wall 301, there are formed a plurality of truncated conical through-holes 305 in a grid pattern. Further, a plurality of rectangular through-holes 306 are formed in both sidewalls 302, the front wall 303 and the rear wall 304. The lid body 300 is shaped in bilateral symmetry. Note, similarly to the first embodiment, the top wall 301 may be provided, at the four corners of the upper face, with hemispherical projections.

The lid body 300 includes a base part 310 arranged on the rear side and a pair of immovable parts 320, 320 and a movable part 330 both arranged on the front side. The movable part 330 is interposed between the left and right immovable parts 320, 320.

Owing to the formation of two slits 307 in the front portion of the lid body 300 while leaving the base part 310 on the rear side of the generally box-shaped lid body 300 thereby to divide the front portion of the lid body 300 into three pieces, there can be provided the immovable part 320 and the movable parts 330 mentioned above. The lid body 300 is made of resinous material and integrally formed by means of a technique such as injection molding. Polyacetal is suitable for the resinous material.

The structure of the base part 310 of the lid body 300 will be described. As shown in FIG. 7, the base part 310 is formed by the respective rear portions of the top wall 301 and both sidewalls 302, and the rear wall 304. Each of the immovable parts 320 is formed by a lateral portion of the front part of the top wall 301, a front portion of the sidewall 302 and a side portion of the front wall 303. The movable part 330 is formed by an intermediate portion of the front part of the top wall 301 and a center portion of the front wall 303.

Therefore, the respective immovable parts 320, 320 are adapted so as to be immovable against the base part 310. While, the movable part 330 is constructed to be movable to the base pat 310, in other words, displaceable against the part 310.

The top wall (part) 301 forming the movable part 330 is curved so as to be gradually apart from a plane containing the top wall (part) 301 forming the base part 310 as approaching the front end of the lid body 300. FIG. 7 shows the lid body 300 in a condition where no external force is applied thereon.

On the lower end of the front wall 301 forming the immovable parts 320, there are provided the front engagement members 221 on the inside of the wall 301 in the left-and-right direction (which are identical to those of the first embodiment) and the tabs 225 on the outside of the wall 301 in the same direction.

Figure 9A:
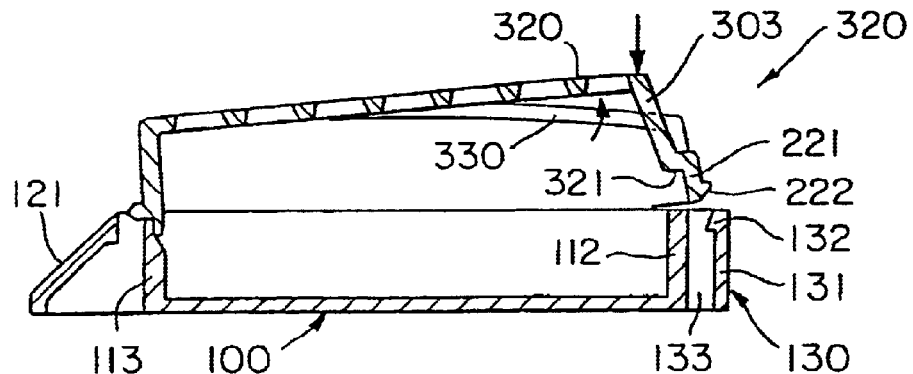
FIG. 9 are sectional views of the sample processing container including an immovable part, for explanation of the operation of the container.

As shown in FIG. 9, the lower end of the front wall 301, which is connected to the front engagement members 221, is bent forward so that an under face of the so that part provides a seat 321 for contact with the top face of the front wall 112 of the container body 100 [see FIG. 9(a)]. The front engagement members 221 are formed to extend downward. As shown in FIG. 7, the tabs 225 are formed to extend forward, so that the under faces of the tabs 225 provide the seats 226 for contact with the top face of the front wall 112 of the container body 100.

As shown in FIG. 7, the front wall 303 forming the movable part 330 is provided with a disengagement part 331. As minutely shown in FIG. 8, the disengagement part 331 is formed by a disengagement member 332 and a supporting member 333 for supporting the disengagement member 332 rotatably. The supporting member 333 is generally U-shaped to have both ends thereof (only one shown in FIG. 8) joined to the front wall 303 forming the movable part 330. The supporting member 333 is coupled to the disengagement member 332 through a thin-walled connecting part 334 in comparison with its environs. Therefore, the disengagement member 332 is capable of rotation about an axis 335 passing through the connecting part 334 in the left-and-right direction (see arrow of FIG. 8).

Figure 8:
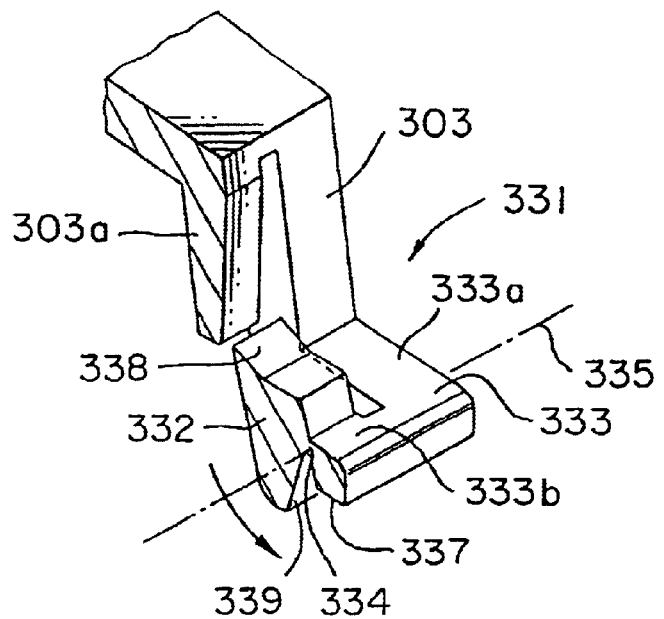
FIG. 8 is a partial sectional view for explanation of the structure of a disengagement part formed on the lid of FIG. 7.

As shown in FIG. 8 and FIG. 11, the under face of a connecting part between a part 333a of the supporting member 333 extending in the front-and-rear direction and the front wall 303 provides a seat 336 for contact with the top face of the front wall 112 of the container body 100. Additionally, the under face of a part 333b of the supporting member 333 extending in the left-and-right direction provides a seat 337 for contact with the top face of the front engagement member 131 of the container body 100.

A member indicated with reference numeral 303a in FIG. 8 is identical to a part of the front wall 303, which is remained to prevent the samples from getting out of the container.

The method of getting the lid body 300 on and off the container body 100 will be described. In the same way as the first embodiment, first insert the rear engagement members 211 into the opening 124 of the container body 100 thereby to engage the step part 122 formed on the slant wall 121 with the engagement claw 212 of the rear engagement member 211.

Subsequently, when putting the lid body 300 on the container body 100, the seats 336, 337 of the movable part 330 being curved downward are respectively seated on the container body 100, so that the front ends of the immovable parts 320 are respectively separated from the front end of the container body 100, realizing the semi-opening condition. That is, the immovable parts 320 and the movable part 330 are brought into the condition shown in FIG. 9(a) and the leading end of the movable part 330, which is eliminated in FIG. 9(a), is seated on the upper faces of the front wall 112 and the front engagement member 131, as shown in FIG. 11 in the rough.

Next, as shown with arrow in FIG. 9(a), the upper face of the front end of the front wall 301 forming the immovable part 320 is depressed downward by means of tweezers etc. (or hand, finger, etc.). Then, the top wall 301 forming the movable part 330 is elastically deformed to change its curved state to the generally flat condition [see arrow of FIG. 9(a)], while the front engagement members 221 at the front end of the immovable parts 320 are engaged with the front engaging part 130 of the container body 100.

Figure 10:
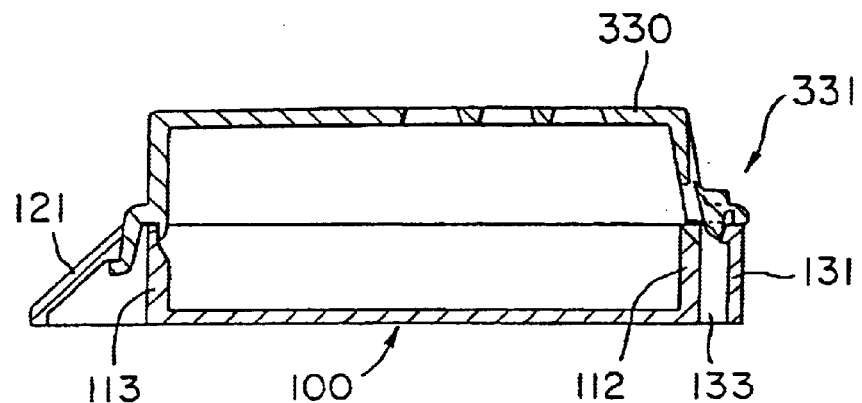
FIG. 10 is a sectional view of the sample processing container including the movable part, for explanation of the operation of the container.
Figure 11A:
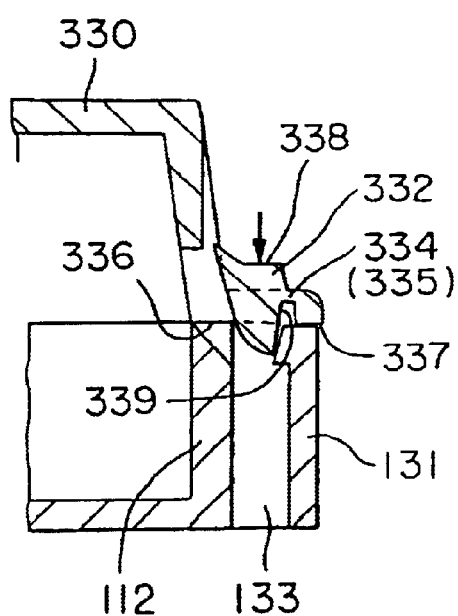
FIG. 11 are sectional views for explanation of the operation of the disengagement part of FIG. 8, showing the right side of FIG. 10 in enlargement.
Figure 11B:
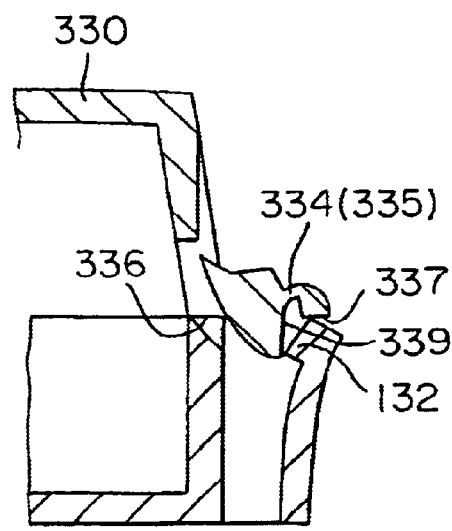

FIGS. 9(a), 10 and 11 illustrate the relationship between the immovable and movable parts 320, 330 and the front engagement part 130 of the container body 100 after the above engagement operation has been completed.

Figure 9B:
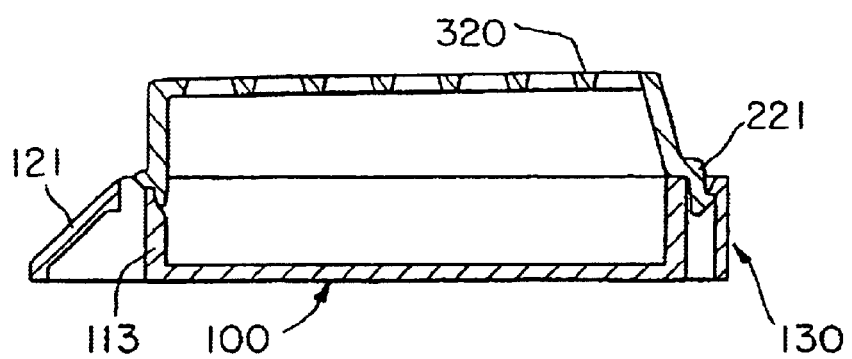

In detail, as shown in FIG. 9(b), the respective seats 321 of the immovable parts 320 are seated on the top face of the front wall 112 of the container body 100, while the seats 226 of the tabs 225 are seated on the top face of the front engagement member 131 (not shown). Then, the front engagement members 221 of the immovable parts 320 are engaged with the front engagement part 130 of the container body 100. (Note, the engaging manner of the front engagement members 221 with the front engagement part 130 is similar to that of the first embodiment.)

The seats 336 of the movable parts 330 is seated on the top face of the front wall 112 of the container body 100, while the seats 337 of the movable part 330 is seated on the top face of the front engagement member 131. Then, the disengagement member 332 enters into the gap 131 between the front wall 112 the container body 100 and the front engagement member 131.

When the engaging operation is completed, the top wall 301 of the lid body 300 forming the movable parts 330 becomes substantially flat, so that the immovable parts 320 and the movable part 330 are generally overlapped with each other in a view of the left-and-right direction. In other words, the portions of the immovable and movable parts 320, 330 formed by the top wall 301 are substantially included in an identical plane. Then, the lid body 300 is turned to be a box whose lower side is opened, performing the function as the lid for concealing the upside of the accommodating part 110 of the container body 100.

Next, we describe an operation to detach the lid body 300 from the container body 100. First, depress a control face 338 of the disengagement member 332 facing substantially upward by tweezers or the like [see arrow of FIG. 11(a)]. As a result, the disengagement member 332 rotates about the axis 335 as its rotation center. Thus, an action face 339 of the disengagement member 332 directing generally forward allows the top end portion of the front engagement member 131 of the container body 100 (i.e. a part of the engagement claw 131 in this embodiment) to move forward [see FIG. 11(b)].

With this movement, there is simultaneously released the engagement between the immovable parts 320 and the front engagement members 131 of the container body 100. As a result, since the top wall 301 forming the movable part 330 intends to be restored by its elasticity, the tips of the immovable parts 320 are separated from the container body 100 to the semi-opening position. Under this situation, it is possible to greatly open the lid body 300 by pinching the tabs 225 of the immovable parts 320 by means of tweezers or the like. By continuously withdrawing the rear engagement members 211 of the lid body 300 out of the opening 124 of the container body 100 while taking the tabs 225 between the tweezers, it allows the lid body 300 to be separated from the container body 100 perfectly.

Also in this embodiment, since the application of a downward force by means of the tweezers allows the lid body 300 to be opened with the user's single action, the sample processing container can exhibit considerably excellent workability.

[3rd. Embodiment]

Next, with reference to FIGS. 12 to 15, the third embodiment of the invention will be described. The third embodiment differs from the first embodiment in that the front side of a lid body is not divided into three and the front engagement member of the container body has a different shape from that of the first embodiment. As to the other constitution, the third embodiment is substantially equal to the first embodiment. Note, in the third embodiment, elements similar to those of the first embodiment are indicated with the same reference numerals respectively and their redundant descriptions are omitted.

As shown in FIGS. 12 and 13, a lid body 200A of this embodiment is in the form of a curved plate. In detail, the lid body 200A is shaped to be a flat plate at the rear area having the projection 213 and also a curved plate at front area. In the modification, the lid body 200A may be curved as a whole.

As similar to the lid body 200 of the first embodiment, the lid body 200 is also provided with the rear engagement member 212 at the rear end and the pair of front engagement members 221 at the front end at a predetermined interval in the left-and-right direction. At the front end of the lid body 200A, a notch 240 is defined between the front engagement members 221 in pairs.

As shown in FIG. 13, a container body 100A of the embodiment includes a front engagement member 131A different from the front engagement member 131 of the container body 100 of the first embodiment, in respect of structure.

That is, the bottom wall 114 of the container body 100A is extended ahead of the front wall 112. The front engagement member 131A stands upright on an extension part 114a of the bottom wall 114 to extend in the left-and-right direction. The front engagement member 131A is partially cut away at its front-and-lower parts on both left and right sides (see reference numeral 140), providing thin-walled portions.

The front engagement member 131A has openings 141, 141 formed for engagement with the engagement claws 222, 222 of the front engagement member 221 of the lid body 200A. Further, the front engagement member 131A is provided, at its top, with a slant face 142.

The front engagement member 131A constructed above is capable of swinging (rotating) about an imaginary axis extending in the left-and-right direction similarly to the front engagement member 131 of the first embodiment. Owing to the swing action of this member, the openings 141 and the vicinities are capable of displacement in the front-and-rear direction.

The constitution of the container body 100A is identical to that of the container body 100 of the first embodiment, except the above-mentioned structure.

Next, the method of getting the lid body 200A on and off the container body 100A will be described. First of all, as similar to the first embodiment, insert the rear engagement members 211 into the opening 124 of the container body 100A thereby to engage the step part 122 formed on the slant wall 121 with the engagement claw 212 of the rear engagement member 211.

In this state, when the lid body 200A is mounted on the top face of the container body 100A, then the rear part of the lid body 200A (corresponding to the base part 210 of the first embodiment) becomes parallel with the opening face of the container body 100A thereby to cover the upside of the accommodating part 110 of the container body 100A. Then, there is established the so-called "semi-opening" condition where the front part of the lid body 200A is apart from the container body 100A (i.e. the front engagement member 131).

Next, the top face of the front end of the lid body 200A is depressed by tweezers, fingers or the like. Consequently, the respective engagement claws 222 of the front engagement members 221 enter into the gap 133 while their slant faces 222a urge the front engagement member 130A forward. After insertion of the claws 222, the front engagement member 131A recover elastically, whereby the respective engagement claws 222 of the front engagement members 221 are engaged in the openings 141 of the front engagement member 131. Note, the under face of the lid body 200A at the front end and the rear faces of the front engagement members 221 are respectively supported by the front wall 112 of the accommodating part 110 of the container body 100A.

In this way, the front engagement members 221 of the lid body 200A are engaged with the front engagement part 130 of the container body 10A, realizing the lid body 200A being in the closed state. Then, the lid body 200 is settled in their elastically-deformed condition and also flattened substantially. In this way, there can be completed an operation to fit the lid body 200A to the container body 100A. When the lid body 200A is fitted to the container body 100A in the above way, the entire lid body 200A becomes a flat plate thereby to cover the upside of the accommodating part 110.

FIG. 15 shows a top view of the front side of the sample processing container in the above-mentioned state. As shown in FIG. 15, owing to the provision of the notch 240 at the front end of the lid body 200A, the gap 133 between the front engagement member 131A and the front wall 112 is exposed, at the area including the notch, to the upward without being covered with the lid body 200A. Therefore, it is possible to insert the tips of the tweezers etc. (i.e. a predetermined tool) into the gap 133 from the upside. In connection, since the front engagement member 131A and the front wall 112 have the slant walls 142, 112a respectively, they allow the tips of the tweezers to be easily inserted into the gap owing to the guide action of the slant walls.

When the tips of the tweezers are inserted into the gap 133, the front engagement member 131A is elastically deformed by the tweezers' wedge action, so that the upper part of the member 131A is displaced in front [see chain line of FIG. 14(b)]. Consequently, the engagement between the claws 222 of the front engagement members 221 and the openings 141 of the front engagement member 131A is released.

Then, since the lid body 200A intends to be restored to the original shape due to its elasticity, the front side of the lid body 200A is separated from the container body 100A as shown with chain line of FIG. 14(b). Thereafter, the lid body 200A can be separated from the container body 100A in the similar way to that of the first embodiment.

Also in this embodiment, since the application of a downward force by means of the tweezers allows the lid body 200A to be opened with the user's single action, the sample processing container can exhibit considerably excellent workability. Additionally, according to the embodiment, it is possible to take effect of simplifying the constitution of the lid body in comparison with the first embodiment.

Although the front wall 112 of the container body 100A is employed as a part of the front engagement part 130 in the above-mentioned embodiment, the present invention is not limited to this arrangement. In the modification, another wall member (i.e. an immovable member) different from the front wall 112 may be arranged so as to oppose the front engagement member 131 at a predetermined interval. In such a case, the front engagement member 221 of the lid body 200 is inserted between the wall member and the front engagement member 131.

[4th. Embodiment]

Next, with reference to FIGS. 16 to 18, the fourth embodiment of the invention will be described. The fourth embodiment differs from the second embodiment in that no disengagement member is arranged in front of the lid body while adopting the container body 100A of the third embodiment. As to the other constitution, the third embodiment is substantially equal to the second embodiment. Note, in the fourth embodiment, elements similar to those of the second (or third) embodiment are indicated with the same reference numerals respectively and their redundant descriptions are omitted.

As shown in FIG. 16, the constitution of a lid body 300A of the embodiment corresponds to a structure obtained as a result of removing the part 333b of the supporting member 333 from the lid body 300 of the second embodiment. Although the supporting member 333 still includes the part 333a of the second embodiment, the same part 333a is remained for only purpose of providing the seat 336 to be seated on the top face of the front wall 112 of the container body 100A.

Next, the method of getting the lid body 300A on and off the container body 100A will be described. The process of fitting the lid body 300A to the container body 100A is substantially identical to that of the second embodiment.

Figure 18:
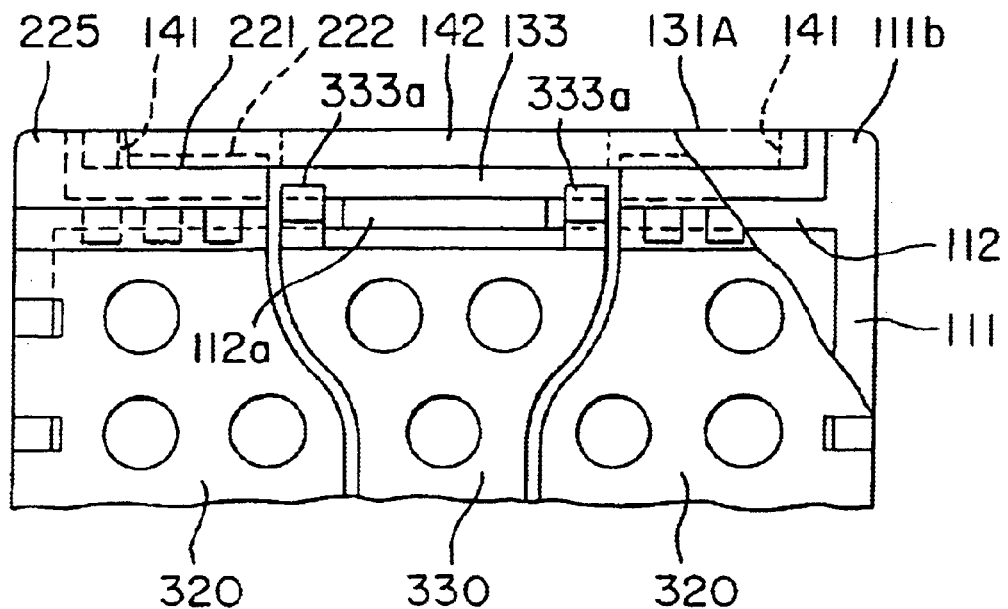
FIG. 18 is top plan view of the sample processing container where the lid is fitted to the container body.

FIG. 17 and FIG. 18 illustrates a condition where the lid body 300A is fitted to the container body 10A. That is, as shown in FIG. 17(a), the front engagement members 221 of the immovable parts 320 enter into the gap 133, so that the claws 222 of the members 221 are engaged with the openings 141 of the front engagement member 131A. Further, as shown in FIG. 17(b), the seat 336 of the movable part 330 is seated on the top face of the front wall 112 of the container body 10A.

FIG. 18 shows a top view of the front side of the sample processing container in the above-mentioned state. As shown in FIG. 18, in front of the movable part 330, the gap 133 between the front engagement member 131A and the front wall 112 is not covered with the lid body 200A but exposed to the upside. Therefore, it is possible to insert the tip of a member, such as tweezers, into the gap 133 from the upside.

When the member such as tweezers is inserted into the gap 133, the front engagement member 131A is displaced to release the engagement between the front engagement member 131A and the front engagement members 221 of the immovable parts 320. Consequently, as similar to the second embodiment, the movable part 330 is restored elastically and the front sides of the immovable parts 320 are separated from the container body 100A. Thereafter, the lid body 300A can be separated from the container body 100A in the similar way to that of the second embodiment.

Also in this embodiment, since the application of a downward force by means of the tweezers allows the lid body 300A to be opened with the user's single action, the sample processing container can exhibit considerably excellent workability. Additionally, according to the embodiment, it is possible to take effect of simplifying the constitution of the lid body in comparison with that of the second embodiment.

As can be understood by the above explanation, the features in common with the first embodiment to the fourth embodiment reside in that the lid body is fitted to the container body while not deforming any component accompanied with the lid body but the lid body's essential part to cover the accommodating part 110 elastically and the lid body can be easily opened by releasing the elastic deformation of the essential part and that the disengagement of the lid body from the container body can be accomplished by only applying a downward force.

Figure 19:
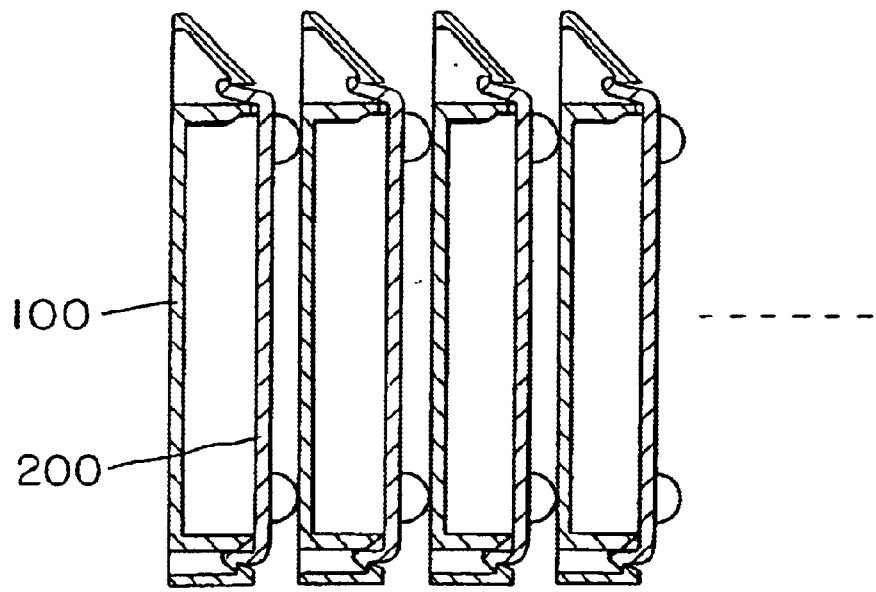
FIG. 19 is a view for explanation of the using method of the sample processing container.

With reference to FIGS. 19 and 20, we now describe a method of processing the samples by the sample processing container. Here at, we describe a method of using the sample processing container in accordance with the first embodiment; nevertheless the method is applicable to the sample processing containers in accordance with the second embodiment to the fourth embodiment of the invention.

First, accommodate the samples (not shown in FIG. 19) in the container body 100 (or the container body 100A) and further fit the lid body 200 (or any one of the lid bodies 200A, 300, 300A). Next, as shown in FIG. 19, stand a plurality of containers in rows. Next, upon fixing these containers by means of bands etc. and dip them into a plurality of processing baths in which various kinds of chemicals are stored, in sequence. In the respective processing baths, a variety of processes (e.g. removal of grease, dehydration, etc.) are applied on the samples while flowing the chemicals in the baths; nevertheless there is no possibility that the chemicals remain in the accommodating part 110 since the container body 100 and the lid body 200 have the great number of through-holes 116, 201 formed therein to allow the chemicals to flow through the accommodating part 110 smoothly. Additionally, owing to the provision of the hemispherical projections 202 in the lid body 200, the sample processing containers can be arranged at appropriate intervals. Therefore, it is possible to make the flow of chemicals more smoothly. When a series of processes are completed, the lid body 200 is detached from the container body 100, so that a sample 401 is transferred into a wrapping dish 400 as shown in FIG. 20(a). Next, as shown in FIG. 20(b), the upside of the wrapping dish 400 is closed up with the container body 100 and thereafter, paraffin 402 is supplied into the dish 400 through the through-holes 116 in the bottom wall 114 of the container body 100.

After the paraffin 402 has gone hard, the wrapping dish 400 is detached from the container body 100, while the body 100 is clamped by a swivel vice (not shown) or the like. In this state, the sample 401 cast in the paraffin 402 is sliced into pieces together with the paraffin 402. Subsequently, the sliced sample (pieces) 410 is further extended and supplied for a microscopic observation while being mounted on a slide glass.

Note, in order to prevent the container body 100 from being distorted at clamping, the through-holes are formed only in the bottom wall 114 of the container body 100 (100A) and are not formed in the other parts of the container body.

What is claimed is:

1. A sample processing container comprising:
    a container body having an accommodating part for accommodating a sample therein, a front engagement part arranged at a front of the accommodating part and a rear engagement part arranged at a rear of the accommodating part; and
    a lid body whereas at least a part thereof is curved, the lid body having a front side and a rear side, the rear side of the lid body being provided with a rear engagement member which is engageable with the rear engagement part of the container body and the front side of the lid body being provided with a rear engagement member which is engageable with the front engagement part of the container body;
    wherein engagement of the front and rear engagement members of the lid body with the front and rear engagement parts of the container body respectively allows the lid body to be fitted to the container body and causes the lid body to be elastically deformed into either a plane state or a reduced-curved state in which a degree of curvature of the lid body is reduced; and
    wherein releasing the engagement of the front engagement member of the lid body with the front engagement part of the container body allows the lid body to be restored elastically, so that the front side of the lid body is separated from the container body, wherein:
        the front engagement part of the container body comprises:
            a front engagement member which extends in a left-and-right direction of the sample processing container and which is elastically displaceable in a front-and-rear direction of the sample processing container and also engageable with the front engagement member of the lid body; and
            an immovable member arranged so that a gap is formed between the front engaging member and the immovable member with respect to the front-and-rear direction;
        when the front engagement member of the lid body is engaged with the front engagement member, the front engagement member is positioned in the gap between the front engagement member and the immovable member of the container body; and
        upon depressing a predetermined member into the gap between the front engagement member and the immovable member, the front engagement member of the container body is displaced in the front-and-rear direction due to a wedge action of the predetermined member, whereby the engagement of the front engagement member of the lid body with the front engagement member of the container body is released.

2. The container according to claim 1, wherein
    the immovable member of the front engagement part of the container body is formed by a front wall defining a front side of the accommodating part of the container body.

3. The container according to claim 1, wherein
    the front engagement member of the container body is capable of swinging about an axis extending in the left-and-right direction, and thus the front engagement member can be displaced in the front-and-rear direction by a swing action of the front engagement member.

4. The container according to claim 1, wherein
    at least a part of gap defined between the front engagement member and the immovable member of the container body is exposed upward without being covered with the lid body when the lid body is fitted to the container body.

5. The container according to claim 4, wherein
    the lid body is provided with a pair of the front engagement members; and
    the gap defined between the front engagement member and the immovable member of the container body is exposed upward between the front engagement members without being covered with the lid body, when the lid body is fitted to the container body.

6. A sample processing container comprising:
    a container body having an accommodating part for accommodating a sample therein, a front engagement part arranged at a front of the accommodating part and a rear engagement part arranged at a rear of the accommodating part; and
    a lid body having a base part provided with a rear engagement member engageable with the rear engagement part of the container body, and first and second movable parts connected in parallel to a front side of the base part with respect to a left-and-right direction of the sample processing container;
    wherein the first movable part is provided with a front engagement member engageable with the front engagement part of the container body, and the second movable part is provided with a disengagement member acting on the front engagement part of the container body thereby to release an engagement between the front engagement part and the front engagement member; and
    wherein the container body and the lid body are configured so that:
        the front engagement member engages with the front engagement part under condition that the first movable part is deformed elastically; and
        when an engagement of the front engagement member with the front engagement part is released by the disengagement member, the first movable part is restored elastically so that the front engagement member is apart from the front engagement part of the container body.

7. The container according to claim 6, wherein:
    the front engagement part of the container body has a front engagement member extending in the left-and-right direction and capable of elastic displacement in a front-and-rear direction;
    the front engagement member is engageable with the front engagement member of the first movable part and capable of displacement by an action of the disengagement member of the second movable part; and the container body and the lid body are configured so that, when the disengagement member of the second movable part butts against the front engagement member of the container body and the disengagement member moves downward, the front engagement member is displaced so that the engagement of the front engagement member of the first movable part with the front engagement part of the container body is released.

8. The container according to claim 7, wherein the front engagement member of the container body is capable of swinging about an axis extending in the left-and-right direction, and thus the front engagement member can be displaced in the front-and-rear direction by a swing action of the front engagement member.

9. The container according to claim 7, wherein:
the disengagement member is formed on an under face of the second movable part and has a slant face; and
when the slant face of the disengagement member butts against the front engagement member of the container body and the disengagement member moves downward, the front engagement member is displaced forward by the slant face, whereby the engagement of the front engagement member of the first movable part with the front engagement part of the container body is released.

10. The container according to claim 6, wherein:
the lid body is formed so as to be a generally flat plate when the lid body is fitted to the container body;
the front part of the lid body is divided into three portions by two slits extending in the front-and-rear direction, an intermediate one of the three portions forming the second movable part shaped to be substantially flat, left and right ones of the three portion forming the first movable part shaped to be curved; and
the rear part of the lid body, which has no slit formed therein, forms the base part.

11. The container according to claim 6, wherein:
the front engagement part of the container body has:
a front wall defining the front side of the accommodating part of the container body; and
and a front engagement member arranged in front of the front wall so that a gap is formed between the front wall and the front engaging member;
the disengagement member is wedge-shaped and is formed on an under face of the second movable part; and
upon depressing the wedge-shaped disengagement member into the gap between the front wall of the accommodating part and the front engagement member, the wedge-shaped disengagement member displaces the front engagement member, whereby the engagement of the front engagement member of the first movable part with the front engagement part of the container body is released.

12. A sample processing container comprising:
a container body having an accommodating part for accommodating a sample therein,
a front engagement part arranged at a front of the accommodating part and a rear engagement part arranged at a rear of the accommodating part; and
a lid body having a base part provided with a rear engagement member engageable with the rear engagement part of the container body, and immovable and movable parts connected in parallel to a front side of the base part with respect to a left-and-right direction, the immovable part being substantially immovable to the base part, the movable part being movable to the base part, the immovable part being provided with a front engagement member which is engageable with the front engagement part of the container body;
wherein the container body and the lid body are configured so that:
upon movement of the immovable part toward the front engagement part of the container body, the immovable part engages with the front engagement part of the container body under condition that the movable part is deformed elastically; and
when an engagement of the front engagement member of the immovable part with the front engagement part of the container body is released by the disengagement member, the movable part is restored elastically so that the front engagement member of the immovable part is apart from the front engagement part of the container body.

13. The container according to claim 12, wherein:
the front engagement part of the container body has:
a front engagement member extending in the left-and-right direction and capable of both elastic displacement in the front-and-rear direction and engagement with the front engagement member of the lid body; and
an immovable member arranged so that a gap is formed between the front engaging member and the immovable member with respect to the front-and-rear direction;
when the front engagement member of the lid body engages with the front engagement member of the container body, the front engagement member is positioned in the gap between the front engagement member and the immovable member of the container body; and
upon depressing a predetermined member into the gap between the front engagement member and the immovable member, the predetermined member displaces the front engagement member of the container body in the front-and-rear direction due to a wedge action of the predetermined member, whereby the engagement of the front engagement member of the lid body with the front engagement member of the container body is released.

14. The sample processing container according to claim 13, wherein the immovable member of the front engagement part of the container body is formed by a front wall defining a front side of the accommodating part of the container body.

15. The container according to claim 13, wherein at least a part of gap defined between the front engagement member and the immovable member of the container body is exposed upward without being covered with the lid body when the lid body is fitted to the container body.

16. The container according to claim 15, wherein the gap defined between the front engagement member and the immovable member of the container body is exposed upward in an area corresponding to the movable part without being covered with the lid body when the lid body is fitted to the container body.

17. The container according to claim 12, wherein the movable part of the lid body is provided with a disengagement member for releasing the engagement between the front engagement part of the container body and the front engagement member of the immovable part.

18. The container according to claim 17, wherein:
the front engagement part of the container body has a front engagement member extending in the left-andright direction and capable of elastic displacement in the front-and-rear direction;

the front engagement member of the immovable part is engageable with the front engagement member of the movable part and capable of displacement by an action of the disengagement member of the movable part; and when the disengagement member of the movable part butts against the front engagement member of the container body and the disengagement member moves, the front engagement member is displaced so that the engagement of the front engagement member of the movable part with the front engagement part of the container body is released.

19. The container according to claim 17, wherein the disengagement member is connected to the movable part so as to be rotatable about an axis extending in the left-and-right direction, and wherein upon depressing the disengagement member downward, the disengagement member displaces the front engagement member of the container body in the front-and-rear direction due to a rotation of the disengagement member.

20. The container according to claim 12, wherein the front engagement member of the container body is capable of swinging about an axis extending in the left-and-right direction, and thus the front engagement member can be displaced in the front-and-rear direction by a swing action of the front engagement member.

21. The container according to claim 12, wherein the lid body is provided with a pair of the immovable parts, and the movable part is arranged between the immovable parts.

22. The container according to claim 21, wherein:

the lid body is substantially box-shaped when the lid body is fitted to the container body;

the front part of the lid body is divided into three parts by two slits extending in the front-and-rear direction, an intermediate one of the three parts forming the movable part, left and right ones of the three parts forming the immovable parts; and the rear part of the lid body, which has no slit formed therein, forms the base part.

23. The container according to claim 22, wherein the lid body configured so that:

when the engagement of the front engagement member of the lid body with the front engagement part of the container body is released, a top wall of each of the immovable parts substantially positioned in a plane including a top wall of the base part; and a top wall of the movable part is curved so as to be gradually apart from the plane including the top wall of the base part according to its proximity of a front end of the lid body.

24. A sample processing container comprising:

a container body having an accommodating part for accommodating a sample therein, a front engagement part arranged at a front of the accommodating part and a rear engagement part arranged at a rear of the accommodating part; and a lid body whereas at least a part thereof is curved, the lid body having a front side and a rear side, the rear side of the lid body being provided with a rear engagement member which is engageable with the rear engagement part of the container body and the front side of the lid body being provided with a rear engagement member which is engageable with the front engagement part of the container body;

wherein engagement of the front and rear engagement members of the lid body with the front and rear engagement parts of the container body respectively allows the lid body to be fitted to the container body and causes the lid body to be elastically deformed into either a plane state or a reduced-curved state in which a degree of curvature of the lid body is reduced; and wherein releasing the engagement of the front engagement member of the lid body with the front engagement part of the container body allows the lid body to be restored elastically, so that the front side of the lid body is separated from the container body, wherein a lid body forms the container, wherein the lid body is in the form of a generally flat plate, said lid body comprising:

a base part arranged on the rear side of the lid body, the base part having a rear on a rear side thereof; and first and second movable parts connected in parallel to a front side of the base part with respect to a left-and-right direction, the first movable part being curved, the second movable part being substantially flat;

wherein the front side of the first movable part is provided with a front engagement member, and a front side of the second movable part is provided with a wedge-shaped member having a slant face.

* * * * *